US010656255B2

(12) United States Patent
Ng et al.

(10) Patent No.: US 10,656,255 B2
(45) Date of Patent: May 19, 2020

(54) PIEZOELECTRIC MICROMACHINED ULTRASONIC TRANSDUCER (PMUT)

(71) Applicant: InvenSense, Inc., San Jose, CA (US)

(72) Inventors: Eldwin Ng, Mountain View, CA (US); Julius Ming-Lin Tsai, San Jose, CA (US); Nikhil Apte, Palo Alto, CA (US)

(73) Assignee: InvenSense, Inc., San Jose, CA (US)

( * ) Notice: Subject to any disclaimer, the term of this patent is extended or adjusted under 35 U.S.C. 154(b) by 363 days.

(21) Appl. No.: 15/205,743

(22) Filed: Jul. 8, 2016

(65) Prior Publication Data

US 2017/0322290 A1 Nov. 9, 2017

Related U.S. Application Data

(60) Provisional application No. 62/331,919, filed on May 4, 2016.

(51) Int. Cl.
*H01L 41/047* (2006.01)
*G01S 7/521* (2006.01)
*B06B 1/06* (2006.01)
*H01L 41/09* (2006.01)
*A61B 5/1172* (2016.01)
*A61B 8/00* (2006.01)
*G01S 15/89* (2006.01)

(52) U.S. Cl.
CPC ............ *G01S 7/521* (2013.01); *A61B 5/1172* (2013.01); *A61B 8/4483* (2013.01); *B06B 1/0622* (2013.01); *G01S 15/89* (2013.01); *H01L 41/047* (2013.01); *H01L 41/0973* (2013.01); *B06B 1/0688* (2013.01)

(58) Field of Classification Search
CPC .......................... H01L 41/047; H01L 41/0973
See application file for complete search history.

(56) References Cited

U.S. PATENT DOCUMENTS

| 5,575,286 A | 11/1996 | Weng et al. |
| 5,684,243 A | 11/1997 | Gururaja et al. |

(Continued)

FOREIGN PATENT DOCUMENTS

| EP | 1214909 A1 | 6/2002 |
| EP | 2884301 A1 | 6/2015 |

(Continued)

OTHER PUBLICATIONS

Tang, et al., "Pulse-Echo Ultrasonic Fingerprint Sensor on a Chip", IEEE Transducers, Anchorage, Alaska, USA, Jun. 21-25, 2015, pp. 674-677.

(Continued)

*Primary Examiner* — Hovhannes Baghdasaryan

(57) ABSTRACT

A Piezoelectric Micromachined Ultrasonic Transducer (PMUT) device is provided. The PMUT includes a substrate and an edge support structure connected to the substrate. A membrane is connected to the edge support structure such that a cavity is defined between the membrane and the substrate, where the membrane is configured to allow movement at ultrasonic frequencies. The membrane includes a piezoelectric layer and first and second electrodes coupled to opposing sides of the piezoelectric layer. An interior support structure is disposed within the cavity and connected to the substrate and the membrane.

30 Claims, 8 Drawing Sheets

(56) References Cited

U.S. PATENT DOCUMENTS

| | | |
|---|---|---|
| 5,808,967 A | 9/1998 | Yu et al. |
| 5,867,302 A | 2/1999 | Fleming |
| 6,071,239 A | 6/2000 | Cribbs et al. |
| 6,104,673 A | 8/2000 | Cole et al. |
| 6,289,112 B1 | 9/2001 | Jain et al. |
| 6,350,652 B1 | 2/2002 | Libera et al. |
| 6,428,477 B1 | 8/2002 | Mason |
| 6,500,120 B1 | 12/2002 | Anthony |
| 6,676,602 B1 | 1/2004 | Barnes et al. |
| 6,736,779 B1 | 5/2004 | Sano et al. |
| 7,067,962 B2 | 6/2006 | Scott |
| 7,109,642 B2 | 9/2006 | Scott |
| 7,243,547 B2 | 7/2007 | Cobianu et al. |
| 7,400,750 B2 | 7/2008 | Nam |
| 7,459,836 B2 | 12/2008 | Scott |
| 7,471,034 B2 | 12/2008 | Schlote-Holubek et al. |
| 7,489,066 B2 | 2/2009 | Scott et al. |
| 7,739,912 B2 | 6/2010 | Schneider et al. |
| 8,018,010 B2 | 9/2011 | Tigli et al. |
| 8,139,827 B2 | 3/2012 | Schneider et al. |
| 8,311,514 B2 | 11/2012 | Bandyopadhyay et al. |
| 8,335,356 B2 | 12/2012 | Schmitt |
| 8,433,110 B2 | 4/2013 | Kropp et al. |
| 8,508,103 B2 | 8/2013 | Schmitt et al. |
| 8,515,135 B2 | 8/2013 | Clarke et al. |
| 8,666,126 B2 | 3/2014 | Lee et al. |
| 8,703,040 B2 | 4/2014 | Liufu et al. |
| 8,723,399 B2 | 5/2014 | Sammoura et al. |
| 8,805,031 B2 | 8/2014 | Schmitt |
| 9,056,082 B2 | 6/2015 | Liautaud et al. |
| 9,070,861 B2 | 6/2015 | Bibl et al. |
| 9,224,030 B2 | 12/2015 | Du et al. |
| 9,245,165 B2 | 1/2016 | Slaby et al. |
| 9,424,456 B1 | 8/2016 | Kamath Koteshwara et al. |
| 9,572,549 B2 | 2/2017 | Belevich et al. |
| 9,582,102 B2 | 2/2017 | Setlak |
| 9,607,203 B1 | 3/2017 | Yazdandoost et al. |
| 9,607,206 B2 | 3/2017 | Schmitt et al. |
| 9,613,246 B1 | 4/2017 | Gozzini et al. |
| 9,665,763 B2 | 5/2017 | Du et al. |
| 9,747,488 B2 | 8/2017 | Yazdandoost et al. |
| 9,785,819 B1 | 10/2017 | Oreifej |
| 9,815,087 B2 | 11/2017 | Ganti et al. |
| 9,817,108 B2 | 11/2017 | Kuo et al. |
| 9,818,020 B2 | 11/2017 | Schuckers et al. |
| 9,881,195 B2 | 1/2018 | Lee et al. |
| 9,881,198 B2 | 1/2018 | Lee et al. |
| 9,898,640 B2 | 2/2018 | Ghavanini |
| 9,904,836 B2 | 2/2018 | Yeke Yazdandoost et al. |
| 9,909,225 B2 | 3/2018 | Lee et al. |
| 9,922,235 B2 | 3/2018 | Cho et al. |
| 9,934,371 B2 | 4/2018 | Hong et al. |
| 9,939,972 B2 | 4/2018 | Shepelev et al. |
| 9,953,205 B1 | 4/2018 | Rasmussen et al. |
| 9,959,444 B2 | 5/2018 | Young et al. |
| 9,967,100 B2 | 5/2018 | Hong et al. |
| 9,983,656 B2 | 5/2018 | Merrell et al. |
| 9,984,271 B1 | 5/2018 | King et al. |
| 10,275,638 B1 | 4/2019 | Yousefpor et al. |
| 10,315,222 B2 | 6/2019 | Salvia et al. |
| 10,600,403 B2 | 3/2020 | Garlepp et al. |
| 2002/0135273 A1 | 9/2002 | Mauchamp et al. |
| 2003/0013955 A1 | 1/2003 | Poland |
| 2004/0085858 A1* | 5/2004 | Khuri-Yakub ........ B06B 1/0688 367/181 |
| 2004/0122316 A1 | 6/2004 | Satoh et al. |
| 2004/0174773 A1 | 9/2004 | Thomenius et al. |
| 2005/0057284 A1 | 3/2005 | Wodnicki |
| 2005/0100200 A1 | 5/2005 | Abiko et al. |
| 2005/0110071 A1 | 5/2005 | Ema et al. |
| 2005/0146240 A1 | 7/2005 | Smith et al. |
| 2005/0148132 A1 | 7/2005 | Wodnicki et al. |
| 2005/0162040 A1 | 7/2005 | Robert |
| 2006/0052697 A1 | 3/2006 | Hossack et al. |
| 2006/0079777 A1 | 4/2006 | Karasawa |
| 2007/0046396 A1 | 3/2007 | Huang |
| 2007/0047785 A1 | 3/2007 | Jang et al. |
| 2007/0073135 A1 | 3/2007 | Lee et al. |
| 2007/0202252 A1 | 8/2007 | Sasaki |
| 2007/0215964 A1 | 9/2007 | Khuri-Yakub et al. |
| 2007/0230754 A1 | 10/2007 | Jain et al. |
| 2008/0125660 A1 | 5/2008 | Yao et al. |
| 2008/0150032 A1 | 6/2008 | Tanaka |
| 2008/0194053 A1* | 8/2008 | Huang ................ B06B 1/0292 438/53 |
| 2008/0240523 A1 | 10/2008 | Benkley et al. |
| 2009/0005684 A1 | 1/2009 | Kristoffersen et al. |
| 2009/0182237 A1 | 7/2009 | Angelsen et al. |
| 2009/0274343 A1 | 11/2009 | Clarke |
| 2009/0303838 A1 | 12/2009 | Svet |
| 2010/0030076 A1 | 2/2010 | Vortman et al. |
| 2010/0046810 A1 | 2/2010 | Yamada |
| 2010/0168583 A1 | 7/2010 | Dausch et al. |
| 2010/0195851 A1 | 8/2010 | Buccafusca |
| 2010/0201222 A1 | 8/2010 | Adachi et al. |
| 2010/0202254 A1* | 8/2010 | Roest .................. B06B 1/0292 367/180 |
| 2010/0239751 A1 | 9/2010 | Regniere |
| 2010/0251824 A1 | 10/2010 | Schneider et al. |
| 2010/0256498 A1 | 10/2010 | Tanaka |
| 2010/0278008 A1 | 11/2010 | Ammar |
| 2011/0285244 A1 | 11/2011 | Lewis et al. |
| 2011/0291207 A1 | 12/2011 | Martin et al. |
| 2012/0016604 A1 | 1/2012 | Irving et al. |
| 2012/0092026 A1 | 4/2012 | Liautaud et al. |
| 2012/0095347 A1 | 4/2012 | Adam et al. |
| 2012/0147698 A1 | 6/2012 | Wong et al. |
| 2012/0232396 A1 | 9/2012 | Tanabe |
| 2012/0238876 A1 | 9/2012 | Tanabe et al. |
| 2012/0279865 A1 | 11/2012 | Regniere et al. |
| 2012/0288641 A1 | 11/2012 | Diatezua et al. |
| 2013/0051179 A1* | 2/2013 | Hong ................... H01L 23/481 367/140 |
| 2013/0064043 A1 | 3/2013 | Degertekin et al. |
| 2013/0127592 A1 | 5/2013 | Fyke et al. |
| 2013/0133428 A1 | 5/2013 | Lee et al. |
| 2013/0201134 A1 | 8/2013 | Schneider et al. |
| 2013/0294202 A1 | 11/2013 | Hajati |
| 2014/0060196 A1 | 3/2014 | Falter et al. |
| 2014/0117812 A1 | 5/2014 | Hajati |
| 2014/0176332 A1 | 6/2014 | Alameh et al. |
| 2014/0208853 A1 | 7/2014 | Onishi et al. |
| 2014/0219521 A1 | 8/2014 | Schmitt et al. |
| 2014/0232241 A1 | 8/2014 | Hajati |
| 2014/0265721 A1* | 9/2014 | Robinson ............. B06B 1/0292 310/300 |
| 2014/0355387 A1 | 12/2014 | Kitchens et al. |
| 2015/0036065 A1 | 2/2015 | Yousefpor et al. |
| 2015/0049590 A1 | 2/2015 | Rowe et al. |
| 2015/0087991 A1 | 3/2015 | Chen et al. |
| 2015/0097468 A1 | 4/2015 | Hajati et al. |
| 2015/0145374 A1 | 5/2015 | Xu et al. |
| 2015/0164473 A1 | 6/2015 | Kim et al. |
| 2015/0165479 A1 | 6/2015 | Lasiter et al. |
| 2015/0169136 A1 | 6/2015 | Ganti et al. |
| 2015/0189136 A1 | 7/2015 | Chung et al. |
| 2015/0198699 A1 | 7/2015 | Kuo et al. |
| 2015/0206738 A1 | 7/2015 | Rastegar |
| 2015/0213180 A1 | 7/2015 | Herberholz |
| 2015/0220767 A1 | 8/2015 | Yoon et al. |
| 2015/0261261 A1 | 9/2015 | Bhagavatula et al. |
| 2015/0286312 A1 | 10/2015 | Kang et al. |
| 2015/0345987 A1 | 12/2015 | Hajati |
| 2016/0051225 A1 | 2/2016 | Kim et al. |
| 2016/0063294 A1 | 3/2016 | Du et al. |
| 2016/0086010 A1 | 3/2016 | Merrell et al. |
| 2016/0092716 A1 | 3/2016 | Yazdandoost et al. |
| 2016/0100822 A1 | 4/2016 | Kim et al. |
| 2016/0107194 A1 | 4/2016 | Panchawagh et al. |
| 2016/0180142 A1 | 6/2016 | Riddle et al. |
| 2016/0326477 A1 | 11/2016 | Fernandez-Alcon et al. |
| 2016/0358003 A1 | 12/2016 | Shen et al. |
| 2017/0330552 A1 | 1/2017 | Garlepp et al. |
| 2017/0075700 A1 | 3/2017 | Abudi et al. |

(56) References Cited

U.S. PATENT DOCUMENTS

| | | |
|---|---|---|
| 2017/0100091 A1 | 4/2017 | Eigil et al. |
| 2017/0110504 A1 | 4/2017 | Panchawagh et al. |
| 2017/0119343 A1 | 5/2017 | Pintoffl |
| 2017/0168543 A1 | 6/2017 | Dai et al. |
| 2017/0185821 A1 | 6/2017 | Chen et al. |
| 2017/0219536 A1 | 8/2017 | Koch et al. |
| 2017/0231534 A1 | 8/2017 | Agassy et al. |
| 2017/0255338 A1 | 9/2017 | Medina et al. |
| 2017/0293791 A1 | 10/2017 | Mainguet et al. |
| 2017/0316243 A1 | 11/2017 | Ghavanini |
| 2017/0322291 A1 | 11/2017 | Salvia et al. |
| 2017/0322292 A1 | 11/2017 | Salvia et al. |
| 2017/0322305 A1 | 11/2017 | Apte et al. |
| 2017/0323133 A1 | 11/2017 | Tsai |
| 2017/0326590 A1 | 11/2017 | Daneman |
| 2017/0326591 A1 | 11/2017 | Apte et al. |
| 2017/0326593 A1 | 11/2017 | Garlepp et al. |
| 2017/0326594 A1 | 11/2017 | Berger et al. |
| 2017/0328866 A1 | 11/2017 | Apte et al. |
| 2017/0328870 A1 | 11/2017 | Garlepp et al. |
| 2017/0330012 A1 | 11/2017 | Salvia et al. |
| 2017/0330553 A1 | 11/2017 | Garlepp et al. |
| 2017/0357839 A1 | 12/2017 | Yazdandoost et al. |
| 2018/0206820 A1 | 7/2018 | Anand et al. |
| 2018/0349663 A1 | 12/2018 | Garlepp et al. |
| 2018/0357457 A1 | 12/2018 | Rasmussen et al. |
| 2018/0369866 A1 | 12/2018 | Sammoura et al. |
| 2019/0005300 A1 | 1/2019 | Garlepp et al. |
| 2019/0102046 A1 | 4/2019 | Miranto et al. |
| 2020/0030850 A1 | 1/2020 | Apte et al. |

FOREIGN PATENT DOCUMENTS

| | | |
|---|---|---|
| JP | 2011040467 A | 2/2011 |
| WO | 2009096576 A2 | 8/2009 |
| WO | 2009137106 A2 | 11/2009 |
| WO | 2014035564 A1 | 3/2014 |
| WO | 2015009635 A1 | 1/2015 |
| WO | 2015112453 A1 | 7/2015 |
| WO | 2015120132 A1 | 8/2015 |
| WO | 2015131083 A1 | 9/2015 |
| WO | 2015183945 A1 | 12/2015 |
| WO | 2016007250 A1 | 1/2016 |
| WO | 2016011172 A1 | 1/2016 |
| WO | 2016040333 A2 | 3/2016 |
| WO | 2017003848 A1 | 1/2017 |
| WO | 2017192895 A1 | 11/2017 |
| WO | 2017196678 A1 | 11/2017 |
| WO | 2017196682 A1 | 11/2017 |
| WO | 2017192903 A3 | 12/2017 |

OTHER PUBLICATIONS

Dausch, et al., "Theory and Operation of 2-D Array Piezoelectric Micromachined Ultrasound Transducers", IEEE Transactions on Ultrasonics, and Frequency Control, vol. 55, No. 11;, Nov. 2008, 2484-2492.

Qiu, et al., "Piezoelectric Micromachined Ultrasound Transducer (PMUT) Arrays for Integrated Sensing, Actuation and Imaging", Sensors 15, doi:10.3390/s150408020, Apr. 3, 2015, 8020-8041.

Savoia, et al., "Design and Fabrication of a cMUT Probe for Ultrasound Imaging of Fingerprints", 2010 IEEE International Ultrasonics Symposium Proceedings, Oct. 2010, 1877-1880.

ISA/EP, International Search Report and Written Opinion for International Application No. PCT/US2017/031140, 18 pages, dated Nov. 2, 2017 (dated Nov. 2, 2017).

ISA/EP, International Search Report for International Application No. PCT/US2017/031826, 16 pages, dated Feb. 27, 2018 (dated Feb. 27, 2018).

ISA/EP, Partial International Search Report for International Application No. PCT/US2017/031823, 12 pages, dated Nov. 30, 2017 (dated Nov. 30, 2017).

ISA/EP, International Search Report and Written Opinion for International Application No. PCT/US2017/031120, 12 pages, dated Aug. 29, 2017 (dated Aug. 29, 2017).

ISA/EP, International Search Report and Written Opinion for International Application No. PCT/US2017/031120, 13 pages, dated Sep. 1, 2017 (dated Sep. 1, 2017).

ISA/EP, International Search Report and Written Opinion for International Application No. PCT/US2017/031134, 12 pages, dated Aug. 30, 2017 (dated Aug. 30, 2017).

ISA/EP, International Search Report and Written Opinion for International Application No. PCT/US2017/031421 13 pages, dated Jun. 21, 2017 (dated Jun. 21, 2017).

ISA/EP, International Search Report and Written Opinion for International Application No. PCT/US2017/031426 13 pages, dated Jun. 22, 2017 (dated Jun. 22, 2017).

ISA/EP, International Search Report and Written Opinion for International Application No. PCT/US2017/031431, 14 pages, dated Aug. 1, 2017 (dated Aug. 1, 2017).

ISA/EP, International Search Report and Written Opinion for International Application No. PCT/US2017/031434, 13 pages, dated Jun. 26, 2017 (dated Jun. 26, 2017).

ISA/EP, International Search Report and Written Opinion for International Application No. PCT/US2017/031439, 10 pages, dated Jun. 20, 2017 (dated Jun. 20, 2017).

ISA/EP, International Search Report and Written Opinion for International Application No. PCT/US2017/031824, 18 pages, dated Sep. 22, 2017 (dated Sep. 22, 2017).

ISA/EP, International Search Report and Written Opinion for International Application No. PCT/US2017/031827, 16 pages, dated Aug. 1, 2017 dated Aug. 1, 2017).

ISA/EP, International Search Report and Written Opinion for International Application No. PCT/US2017/031831, 12 pages, dated Jul. 21, 2017 (dated Jul. 21, 2017).

ISA/EP, Partial International Search Report for International Application No. PCT/US2017/031140, 13 pages, dated Aug. 29, 2017 (dated Aug. 29, 2017).

Hopcroft, et al., "Temperature Compensation of a MEMS Resonator Using Quality Factor as a Thermometer", Retrieved from Internet: http://micromachine.stanford.edu/~amanu/linked/MAH_MEMS2006.pdf, 2006, 222-225.

Hopcroft, et al., "Using the temperature dependence of resonator quality factor as a thermometer", Applied Physics Letters 91. Retrieved from Internet: http://micromachine.stanford.edu/~hoperoft/Publications/Hoperoft_QT_ApplPhysLett_91_013505.pdf, 2007, 013505-1-031505-3.

Lee, et al., "Low jitter and temperature stable MEMS oscillators", Frequency Control Symposium (FCS), 2012 IEEE International, May 2012, 1-5.

Li, et al., "Capacitive micromachined ultrasonic transducer for ultra-low pressure measurement: Theoretical study", AIP Advances 5.12. Retrieved from Internet: http://scitation.aip.org/content/aip/journal/adva/5/12/10.1063/1.4939217, 2015, 127231.

Rozen, et al., "Air-Coupled Aluminum Nitride Piezoelectric Micromachined Ultrasonic Transducers at 0.3 Mhz to 0.9 Mhz", 2015 28th IEEE International Conference on Micro Electro Mechanical Systems (MEMS), IEEE, Jan. 18, 2015, 921-924.

Shen, et al., "Anisotropic Complementary Acoustic Metamaterial for Canceling out Aberrating Layers", American Physical Society, Physical Review X 4.4: 041033., Nov. 19, 2014, 041033-1—041033-7.

Thakar, et al., "Multi-resonator approach to eliminating the temperature dependence of silicon-based timing references", Hilton Head'14. Retrieved from the Internet: http://blog.narotama.ac.id/wp-content/uploads/2014/12/Multi-resonator-approach-to-eliminating-the-temperature-dependance-of-silicon-based-timing-references.pdf, 2014, 415-418.

"ISA/EP, International Search Report and Written Opinion for International Application # PCT/US2018/063431, pp. 1-15, dated Feb. 5, 2019 (dated Feb. 5, 2019))".

"Moving Average Filters", Waybackmachine XP05547422, Retrieved from the Internet: URL:https://web.archive.org/web/20170809081353/

(56) References Cited

OTHER PUBLICATIONS https//www.analog.com/media/en/technical-documentation/dsp-book/dsp_book_Ch15.pdf—[retrieved on Jan. 24, 2019], Aug. 9, 2017, 1-8.
"Receiver Thermal Noise Threshold", Fisher Telecommunication Services, Satellite Communications. Retrieved from the Internet: URL:https://web.archive.org/web/20171027075705/http//www.fishercom.xyz:80/satellite-communications/receiver-thermal-noise-threshold.html, Oct. 27, 2017, 3.
"Sleep Mode", Wikipedia, Retrieved from the Internet: URL:https://web.archive.org/web/20170908153323/https://en.wikipedia.org/wiki/Sleep_mode [retrieved on Jan. 25, 2019], Sep. 8, 2017, 1-3.
"TMS320C5515 Fingerprint Development Kit (FDK) Hardware Guide", Texas Instruments, Literature No. SPRUFX3, XP055547651, Apr. 2010, 1-26.
"ZTE V7 MAX. 5,5" smartphone on MediaTeck Helio P10 cpu; Published on Apr. 20, 2016; https://www.youtube.com/watch?v=ncNCbpkGQzU (Year: 2016)".
ISA/EP, Partial International Search Report for International Application No. PCT/US2019/034032, 8 pages, dated Sep. 12, 2019, 8.
ISA/EP, International Search Report and Written Opinion for International Application # PCT/US2019/015020, pp. 1-23, dated Jul. 1, 2019.
ISA/EP, International Search Report and Written Opinion for International Application # PCT/US2019/023440, pp. 1-10, dated Jun. 4, 2019.
Cappelli, et al., "Fingerprint Image Reconstruction from Standard Templates", IEEE Transactions on Pattern Analysis and Machine Intelligence, IEEE Computer Society, vol. 29, No. 9, Sep. 2007, 1489-1503.
Feng, et al., "Fingerprint Reconstruction: From Minutiae to Phase", IEEE Transactions on Pattern Analysis and Machine Intelligence, IEEE Computer Society, vol. 33, No. 2, Feb. 2011, 209-223.
Kumar, et al., "Towards Contactless, Low-Cost and Accurate 3D Fingerprint Identification", IEEE Transactions on Pattern Analysis and Machine Intelligence, IEEE Computer Society, vol. 37, No. 3, Mar. 2015, 681-696.
Pang, et al., "Extracting Valley-Ridge Lines from Point-Cloud-Based 3D Fingerprint Models", IEEE Computer Graphics and Applications, IEEE Service Center, New York, vol. 33, No. 4, Jul./Aug. 2013, 73-81.
Papageorgiou, et al., "Self-Calibration of Ultrasonic Transducers in an Intelligent Data Acquisition System", International Scientific Journal of Computing, 2003, vol. 2, Issue 2 Retrieved Online: URL: https://scholar.google.com/scholar?q=self-calibration+of+ultrasonic+transducers+in+an+intelligent+data+acquisition+system&hl=en&as_sdt=0&as_vis=1&oi=scholart, 2003, 9-15.
Ross, et al., "From Template to Image: Reconstructing Fingerprints from Minutiae Points", IEEE Transactions on Pattern Analysis and Machine Intelligence, IEEE Computer Society, vol. 29, No. 4, Apr. 2007, 544-560.
Zhou, et al., "Partial Fingerprint Reconstruction with Improved Smooth Extension", Network and System Security, Springer Berlin Heidelberg, Jun. 3, 2013, 756-762.

* cited by examiner

PIEZOELECTRIC MICROMACHINED ULTRASONIC TRANSDUCER (PMUT)

RELATED APPLICATIONS

This application claims priority to and the benefit of U.S. Patent Provisional Patent Application 62/331,919, filed on May 4, 2016, entitled "PINNED ULTRASONIC TRANSDUCERS," by Ng et al., and assigned to the assignee of the present application, which is incorporated herein by reference in its entirety.

BACKGROUND

Piezoelectric materials facilitate conversion between mechanical energy and electrical energy. Moreover, a piezoelectric material can generate an electrical signal when subjected to mechanical stress, and can vibrate when subjected to an electrical voltage. Piezoelectric materials are widely utilized in piezoelectric ultrasonic transducers to generate acoustic waves based on an actuation voltage applied to electrodes of the piezoelectric ultrasonic transducer.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

DESCRIPTION OF EMBODIMENTS

Figure 1:
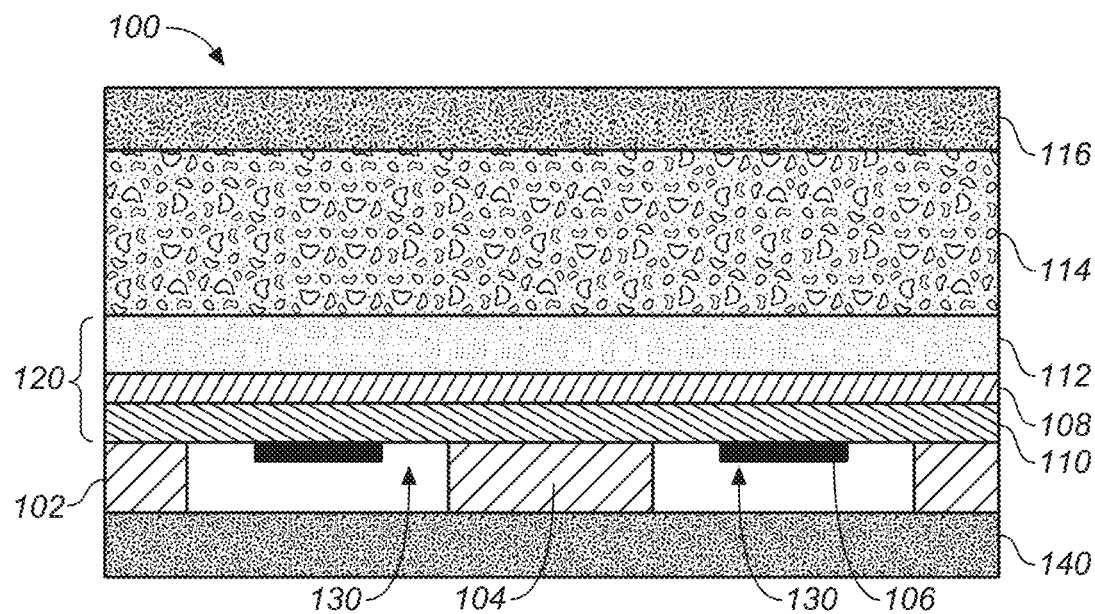
FIG. 1 is a diagram illustrating a PMUT device having a center pinned membrane, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "transmitting," "receiving," "sensing," "generating," "imaging," or the like, refer to the actions and processes of an electronic device such as an electrical device.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example fingerprint sensing system and/or mobile electronic device described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

OVERVIEW OF DISCUSSION

Discussion begins with a description of an example piezoelectric micromachined ultrasonic transducer (PMUT), in accordance with various embodiments. Example arrays including PMUT devices are then described. Example operations of the example arrays of PMUT devices are then further described.

A conventional piezoelectric ultrasonic transducer able to generate and detect pressure waves can include a membrane with the piezoelectric material, a supporting layer, and electrodes combined with a cavity beneath the electrodes. Miniaturized versions are referred to as PMUTs. Typical PMUTs use an edge anchored membrane or diaphragm that maximally oscillates at or near the center of the membrane at a resonant frequency (f) proportional to $h/a^2$, where h is the thickness, and a is the radius of the membrane. Higher frequency membrane oscillations can be created by increasing the membrane thickness, decreasing the membrane radius, or both. Increasing the membrane thickness has its limits, as the increased thickness limits the displacement of the membrane. Reducing the PMUT membrane radius also has limits, because a larger percentage of PMUT membrane area is used for edge anchoring.

Embodiments describes herein relate to a PMUT device for ultrasonic wave generation and sensing. In accordance with various embodiments, an array of such PMUT devices is described. The PMUT includes a substrate and an edge support structure connected to the substrate. A membrane is connected to the edge support structure such that a cavity is defined between the membrane and the substrate, where the membrane is configured to allow movement at ultrasonic frequencies. The membrane includes a piezoelectric layer and first and second electrodes coupled to opposing sides of the piezoelectric layer. An interior support structure is disposed within the cavity and connected to the substrate and the membrane.

The described PMUT device and array of PMUT devices can be used for generation of acoustic signals or measurement of acoustically sensed data in various applications, such as, but not limited to, medical applications, security systems, biometric systems (e.g., fingerprint sensors and/or motion/gesture recognition sensors), mobile communication systems, industrial automation systems, consumer electronic devices, robotics, etc. In one embodiment, the PMUT device can facilitate ultrasonic signal generation and sensing (transducer). Moreover, embodiments describe herein provide a sensing component including a silicon wafer having a two-dimensional (or one-dimensional) array of ultrasonic transducers.

Embodiments described herein provide a PMUT that operates at a high frequency for reduced acoustic diffraction through high acoustic velocity materials (e.g., glass, metal), and for shorter pulses so that spurious reflections can be time-gated out. Embodiments described herein also provide a PMUT that has a low quality factor providing a shorter ring-up and ring-down time to allow better rejection of spurious reflections by time-gating. Embodiments described herein also provide a PMUT that has a high fill-factor providing for large transmit and receive signals.

Piezoelectric Micromachined Ultrasonic Transducer (PMUT)

Systems and methods disclosed herein, in one or more aspects provide efficient structures for an acoustic transducer (e.g., a piezoelectric actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

FIG. 1 is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections the sides or in vias through edge support 102 or interior support 104, electrically coupling lower electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes lower electrode 106, piezoelectric layer 110, and upper electrode 108, where lower electrode 106 and upper electrode 108 are coupled to opposing sides of piezoelectric layer 110. As shown, lower electrode 106 is coupled to a lower surface of piezoelectric layer 110 and upper electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 140 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 2:
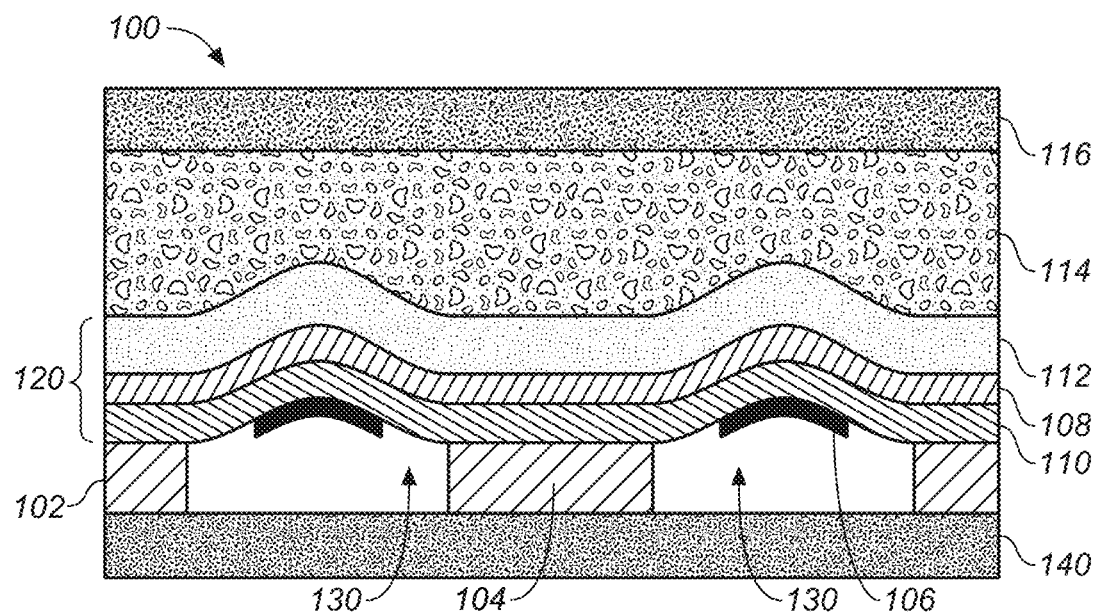
FIG. 2 is a diagram illustrating an example of membrane movement during activation of a PMUT device, according to some embodiments.

FIG. 2 is a diagram illustrating an example of membrane movement during activation of PMUT device 100, according to some embodiments. As illustrated with respect to FIG. 2, in operation, responsive to an object proximate platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to) distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, Aluminum nitride (AlN), lead zirconate titanate (PZT), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Figure 10:
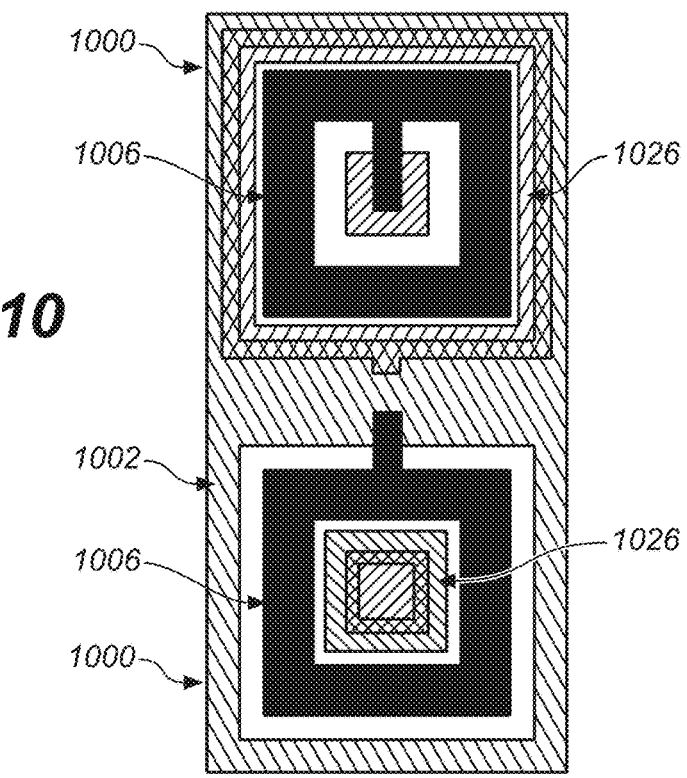
FIG. 10 illustrates an example pair of PMUT devices in a PMUT array, with each PMUT having differing electrode patterning, according to some embodiments.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, electrode 106 is a patterned electrode and electrode 108 is a continuous electrode. As an example, electrodes 106 and 108 can be comprised of almost any metal layers, such as, but not limited to, Aluminum (Al)/Titanium (Ti), Molybdenum (Mo), etc., which are coupled with an on opposing sides of the piezoelectric layer 110. In one embodiment, PMUT device also includes a third electrode, as illustrated in FIG. 10 and described below.

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 MRayl, such as, but not limited to, plastic, resin, rubber, Teflon, epoxy, etc. In another example, the platen layer 116 can comprise various materials having a high acoustic impedance (e.g., an acoustic impendence greater than 10 MiRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$ Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, MN, Titanium nitride (TiN), Silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., Aluminum (Al)/Titanium (Ti), Molybdenum (Mo), etc.) patterned to form electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, electrode 108 can be formed as a continuous layer providing a ground plane in contact with mechanical support layer 112, which can be formed from silicon or other suitable mechanical stiffening material. In still other embodiments, the electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

Figure 3:
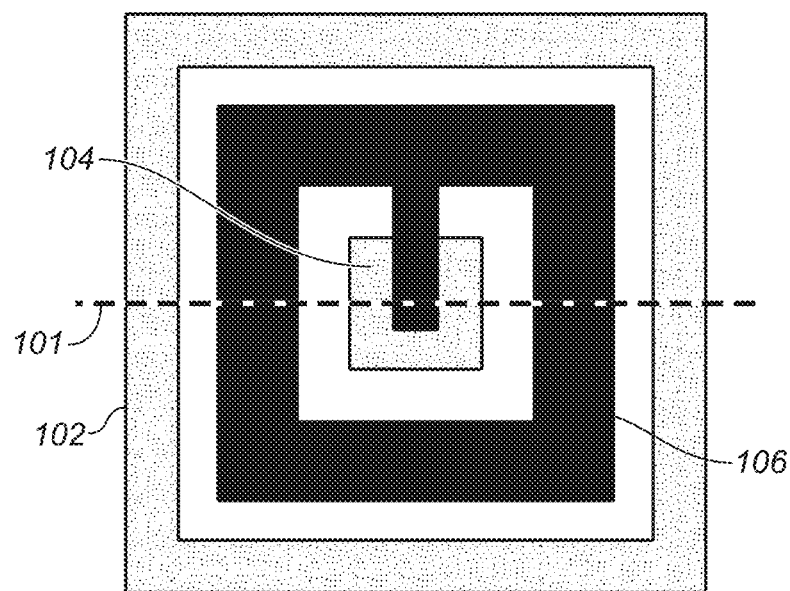
FIG. 3 is a top view of the PMUT device of FIG. 1, according to some embodiments.

FIG. 3 is a top view of the PMUT device 100 of FIG. 1 having a substantially square shape, which corresponds in part to a cross section along dotted line 101 in FIG. 3. Layout of surrounding edge support 102, interior support 104, and lower electrode 106 are illustrated, with other continuous layers not shown. It should be appreciated that the term "substantially" in "substantially square shape" is intended to convey that a PMUT device 100 is generally square-shaped, with allowances for variations due to manufacturing processes and tolerances, and that slight deviation from a square shape (e.g., rounded corners, slightly wavering lines, deviations from perfectly orthogonal corners or intersections, etc.) may be present in a manufactured device. While a generally square arrangement PMUT device is shown, alternative embodiments including rectangular, hexagon, octagonal, circular, or elliptical are contemplated. In other embodiments, more complex electrode or PMUT device shapes can be used, including irregular and non-symmetric layouts such as chevrons or pentagons for edge support and electrodes.

Figure 4:
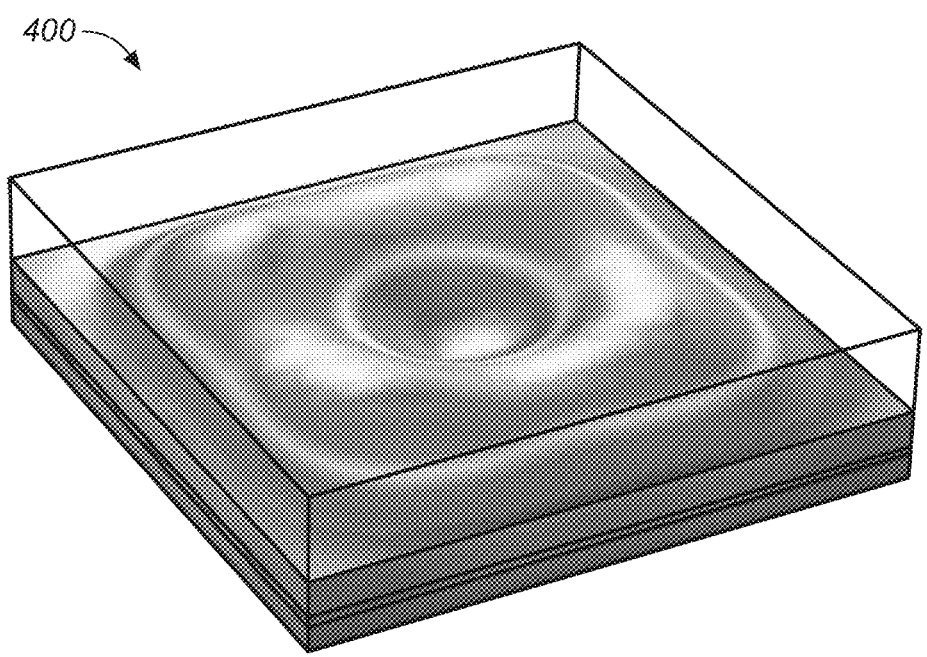
FIG. 4 is a simulated map illustrating maximum vertical displacement of the membrane of the PMUT device shown in FIGS. 1-3, according to some embodiments.

FIG. 4 is a simulated topographic map 400 illustrating maximum vertical displacement of the membrane 120 of the PMUT device 100 shown in FIGS. 1-3. As indicated, maximum displacement generally occurs along a center axis of the lower electrode, with corner regions having the greatest displacement. As with the other figures, FIG. 4 is not drawn to scale with the vertical displacement exaggerated for illustrative purposes, and the maximum vertical displacement is a fraction of the horizontal surface area comprising the PMUT device 100. In an example PMUT device 100, maximum vertical displacement may be measured in nanometers, while surface area of an individual PMUT device 100 may be measured in square microns.

Figure 5:
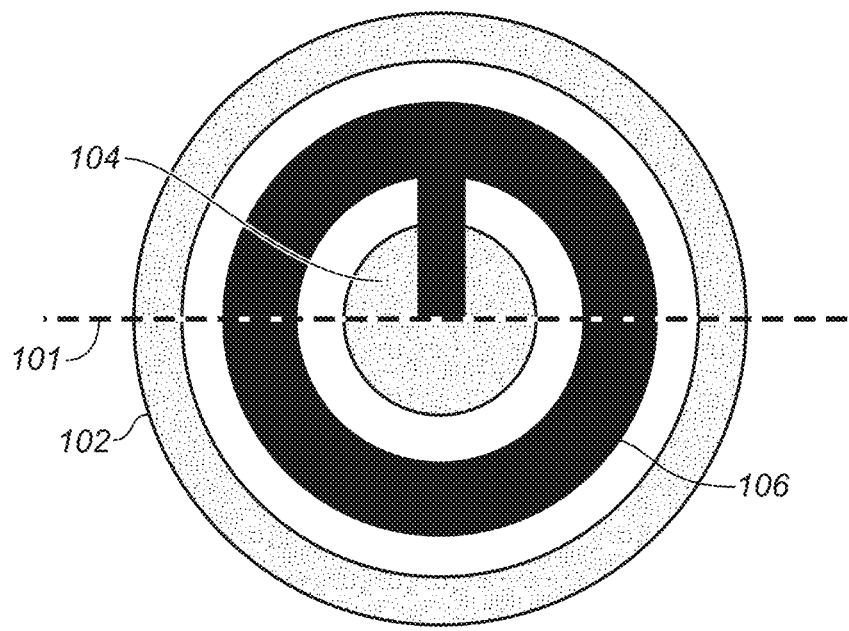
FIG. 5 is a top view of an example PMUT device having a circular shape, according to some embodiments.

FIG. 5 is a top view of another example of the PMUT device 100 of FIG. 1 having a substantially circular shape, which corresponds in part to a cross section along dotted line 101 in FIG. 5. Layout of surrounding edge support 102, interior support 104, and lower electrode 106 are illustrated, with other continuous layers not shown. It should be appreciated that the term "substantially" in "substantially circular shape" is intended to convey that a PMUT device 100 is generally circle-shaped, with allowances for variations due to manufacturing processes and tolerances, and that slight deviation from a circle shape (e.g., slight deviations on radial distance from center, etc.) may be present in a manufactured device.

Figure 6:
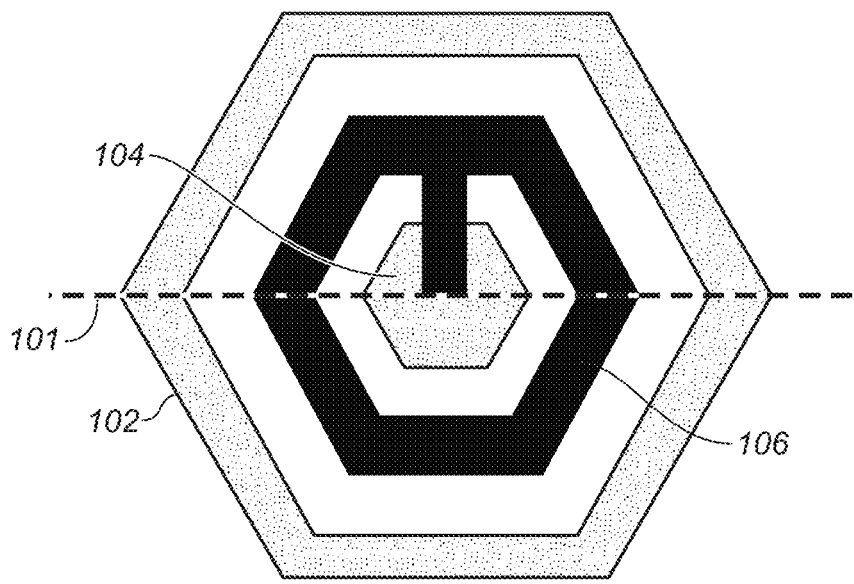
FIG. 6 is a top view of an example PMUT device having a hexagonal shape, according to some embodiments.

FIG. 6 is a top view of another example of the PMUT device 100 of FIG. 1 having a substantially hexagonal shape, which corresponds in part to a cross section along dotted line 101 in FIG. 6. Layout of surrounding edge support 102, interior support 104, and lower electrode 106 are illustrated, with other continuous layers not shown. It should be appreciated that the term "substantially" in "substantially hexagonal shape" is intended to convey that a PMUT device 100 is generally hexagon-shaped, with allowances for variations due to manufacturing processes and tolerances, and that slight deviation from a hexagon shape (e.g., rounded corners, slightly wavering lines, deviations from perfectly orthogonal corners or intersections, etc.) may be present in a manufactured device.

Figure 7:
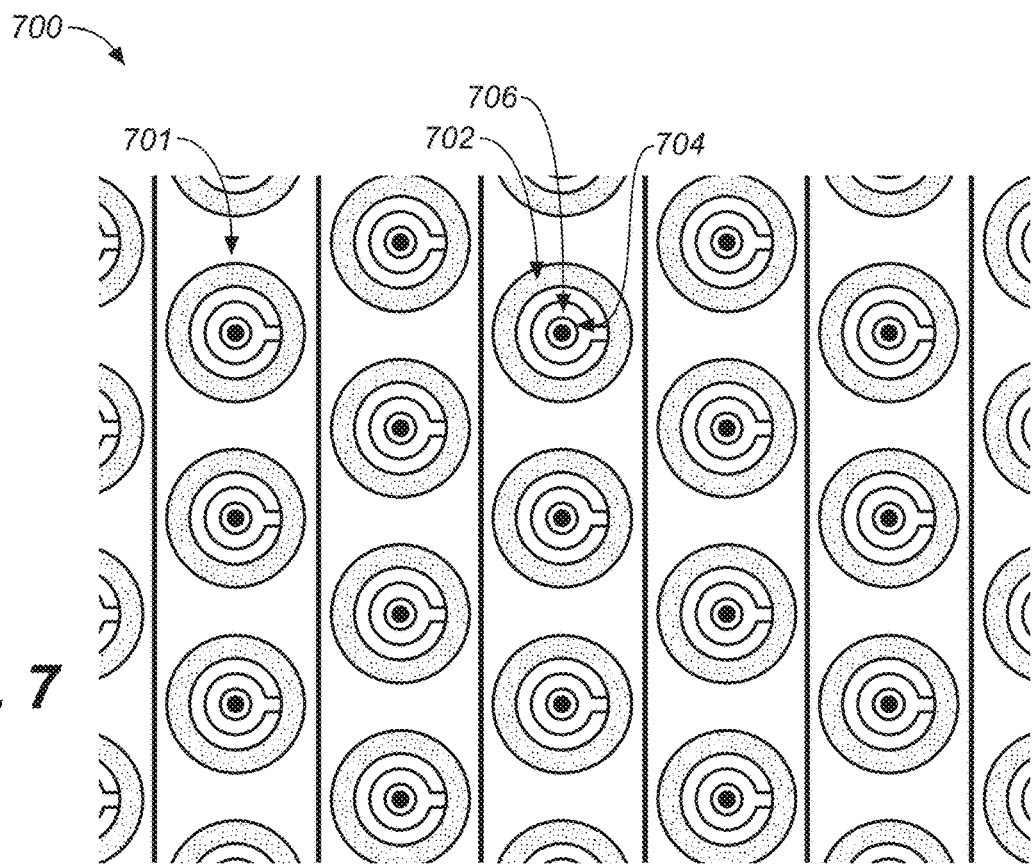
FIG. 7 illustrates an example array of circular-shaped PMUT devices, according to some embodiments.

FIG. 7 illustrates an example two-dimensional array 700 of circular-shaped PMUT devices 701 formed from PMUT devices having a substantially circular shape similar to that discussed in conjunction with FIGS. 1, 2 and 5. Layout of circular surrounding edge support 702, interior support 704, and annular or ring shaped lower electrode 706 surrounding the interior support 704 are illustrated, while other continuous layers are not shown for clarity. As illustrated, array 700 includes columns of circular-shaped PMUT devices 701 that are offset. It should be appreciated that the circular-shaped PMUT devices 701 may be closer together, such that edges of the columns of circular-shaped PMUT devices 701 overlap. Moreover, it should be appreciated that circular-shaped PMUT devices 701 may contact each other. In various embodiments, adjacent circular-shaped PMUT devices 701 are electrically isolated. In other embodiments, groups of adjacent circular-shaped PMUT devices 701 are electrically connected, where the groups of adjacent circular-shaped PMUT devices 701 are electrically isolated.

Figure 8:
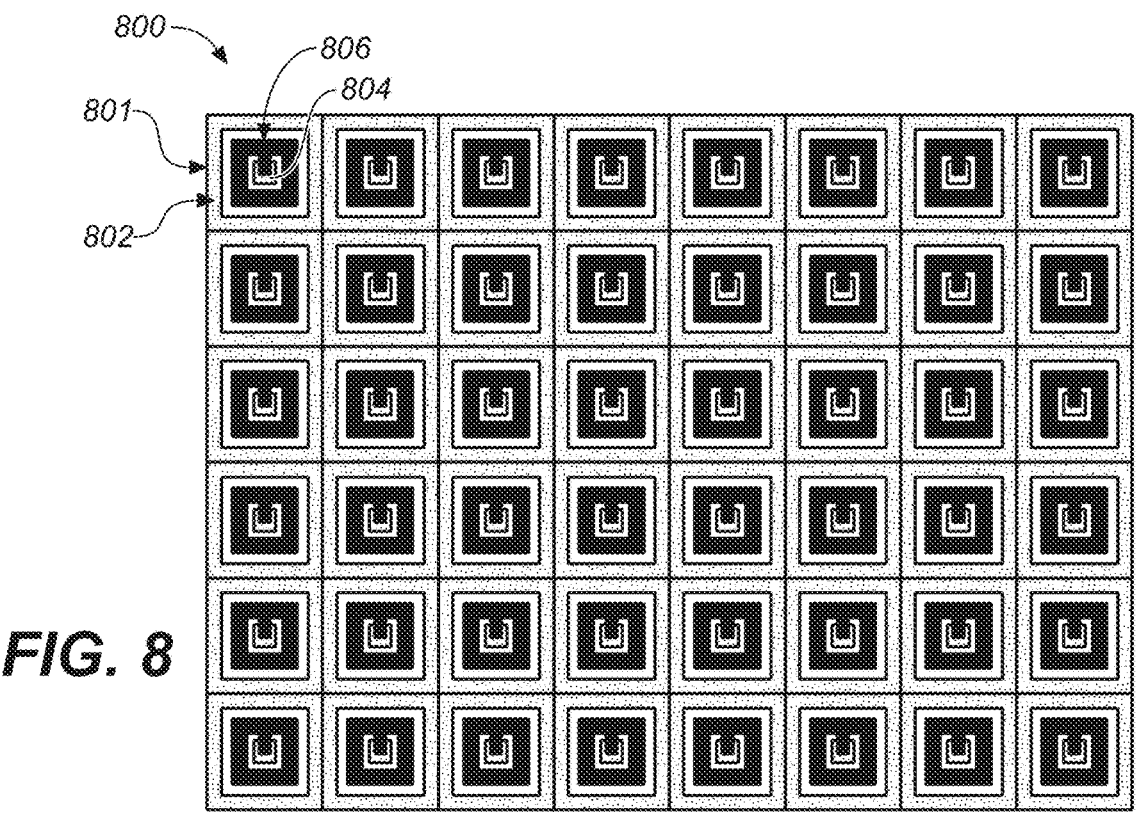
FIG. 8 illustrates an example array of square-shaped PMUT devices, according to some embodiments.

FIG. 8 illustrates an example two-dimensional array 800 of square-shaped PMUT devices 801 formed from PMUT devices having a substantially square shape similar to that discussed in conjunction with FIGS. 1, 2 and 3. Layout of square surrounding edge support 802, interior support 804, and square-shaped lower electrode 806 surrounding the interior support 804 are illustrated, while other continuous layers are not shown for clarity. As illustrated, array 800 includes columns of square-shaped PMUT devices 801 that are in rows and columns. It should be appreciated that rows or columns of the square-shaped PMUT devices 801 may be offset. Moreover, it should be appreciated that square-shaped PMUT devices 801 may contact each other or be spaced apart. In various embodiments, adjacent square-shaped PMUT devices 801 are electrically isolated. In other embodiments, groups of adjacent square-shaped PMUT devices 801 are electrically connected, where the groups of adjacent square-shaped PMUT devices 801 are electrically isolated.

Figure 9:
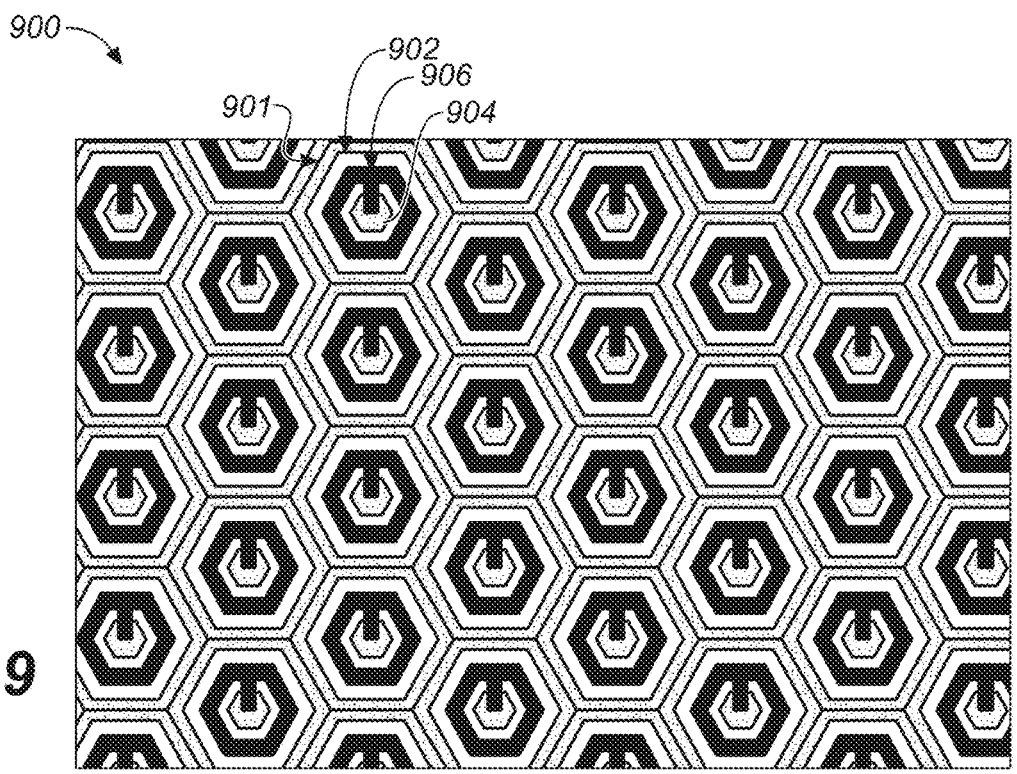
FIG. 9 illustrates an example array of hexagonal-shaped PMUT devices, according to some embodiments.

FIG. 9 illustrates an example two-dimensional array 900 of hexagon-shaped PMUT devices 901 formed from PMUT devices having a substantially hexagon shape similar to that discussed in conjunction with FIGS. 1, 2 and 6. Layout of hexagon-shaped surrounding edge support 902, interior support 904, and hexagon-shaped lower electrode 906 surrounding the interior support 904 are illustrated, while other continuous layers are not shown for clarity. It should be appreciated that rows or columns of the hexagon-shaped PMUT devices 901 may be offset. Moreover, it should be appreciated that hexagon-shaped PMUT devices 901 may contact each other or be spaced apart. In various embodiments, adjacent hexagon-shaped PMUT devices 901 are electrically isolated. In other embodiments, groups of adjacent hexagon-shaped PMUT devices 901 are electrically connected, where the groups of adjacent hexagon-shaped PMUT devices 901 are electrically isolated. While FIGS. 7, 8 and 9 illustrate example layouts of PMUT devices having different shapes, it should be appreciated that many different layouts are available. Moreover, in accordance with various embodiments, arrays of PMUT devices are included within a MEMS layer.

In operation, during transmission, selected sets of PMUT devices in the two-dimensional array can transmit an acoustic signal (e.g., a short ultrasonic pulse) and during sensing, the set of active PMUT devices in the two-dimensional array can detect an interference of the acoustic signal with an object (in the path of the acoustic wave). The received interference signal (e.g., generated based on reflections, echoes, etc. of the acoustic signal from the object) can then be analyzed. As an example, an image of the object, a distance of the object from the sensing component, a density of the object, a motion of the object, etc., can all be determined based on comparing a frequency and/or phase of the interference signal with a frequency and/or phase of the acoustic signal. Moreover, results generated can be further analyzed or presented to a user via a display device (not shown).

FIG. 10 illustrates a pair of example PMUT devices 1000 in a PMUT array, with each PMUT sharing at least one common edge support 1002. As illustrated, the PMUT devices have two sets of independent lower electrode labeled as 1006 and 1026. These differing electrode patterns enable antiphase operation of the PMUT devices 1000, and increase flexibility of device operation. In one embodiment, the pair of PMUTs may be identical, but the two electrodes could drive different parts of the same PMUT antiphase (one contracting, and one extending), such that the PMUT displacement becomes larger. While other continuous layers are not shown for clarity, each PMUT also includes an upper electrode (e.g., upper electrode 108 of FIG. 1). Accordingly, in various embodiments, a PMUT device may include at least three electrodes.

FIGS. 11A, 11B, 11C, and 11D illustrate alternative examples of interior support structures, in accordance with various embodiments. Interior supports structures may also be referred to as "pinning structures," as they operate to pin the membrane to the substrate. It should be appreciated that interior support structures may be positioned anywhere within a cavity of a PMUT device, and may have any type of shape (or variety of shapes), and that there may be more than one interior support structure within a PMUT device. While FIGS. 11A, 11B, 11C, and 11D illustrate alternative examples of interior support structures, it should be appreciated that these examples or for illustrative purposes, and are not intended to limit the number, position, or type of interior support structures of PMUT devices.

Figure 11A:
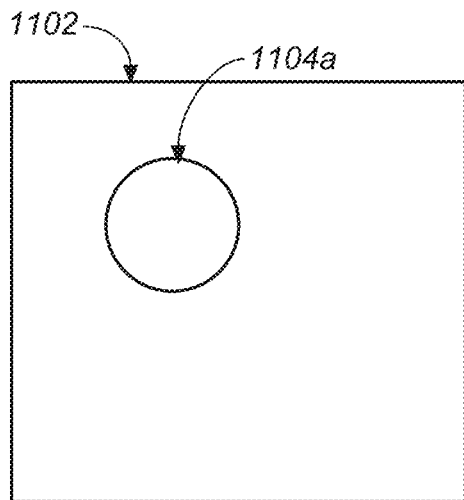
FIGS. 11A, 11B, 11C, and 11D illustrate alternative examples of interior support structures, according to various embodiments.
Figure 11B:
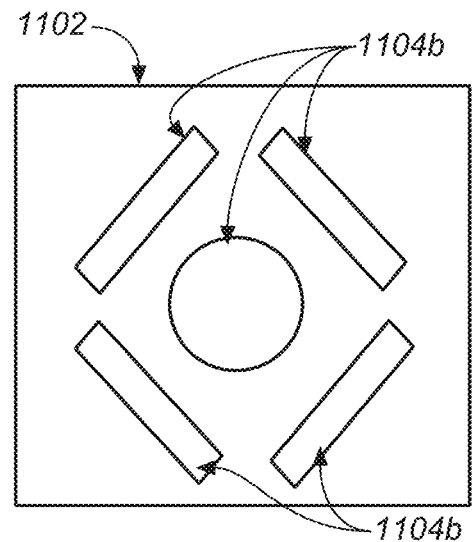
Figure 11C:
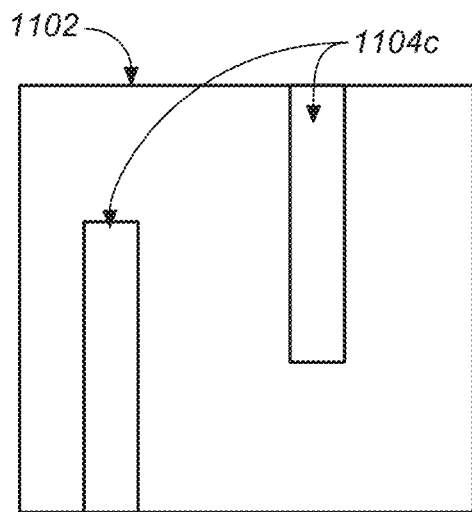
Figure 11D:
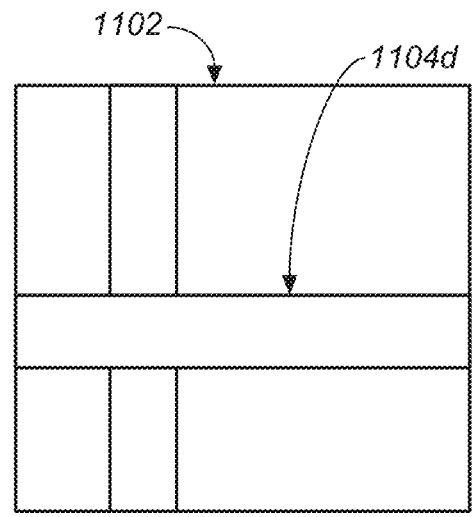

For example, interior supports structures do not have to be centrally located with a PMUT device area, but can be non-centrally positioned within the cavity. As illustrated in FIG. 11A, interior support 1104a is positioned in a non-central, off-axis position with respect to edge support 1102. In other embodiments such as seen in FIG. 11B, multiple interior supports 1104b can be used. In this embodiment, one interior support is centrally located with respect to edge support 1102, while the multiple, differently shaped and sized interior supports surround the centrally located support. In still other embodiments, such as seen with respect to FIGS. 11C and 11D, the interior supports (respectively 1104c and 1104d) can contact a common edge support 1102. In the embodiment illustrated in FIG. 11D, the interior supports 1104d can effectively divide the PMUT device into subpixels. This would allow, for example, activation of smaller areas to generate high frequency ultrasonic waves, and sensing a returning ultrasonic echo with larger areas of the PMUT device. It will be appreciated that the individual pinning structures can be combined into arrays.

Figure 12:
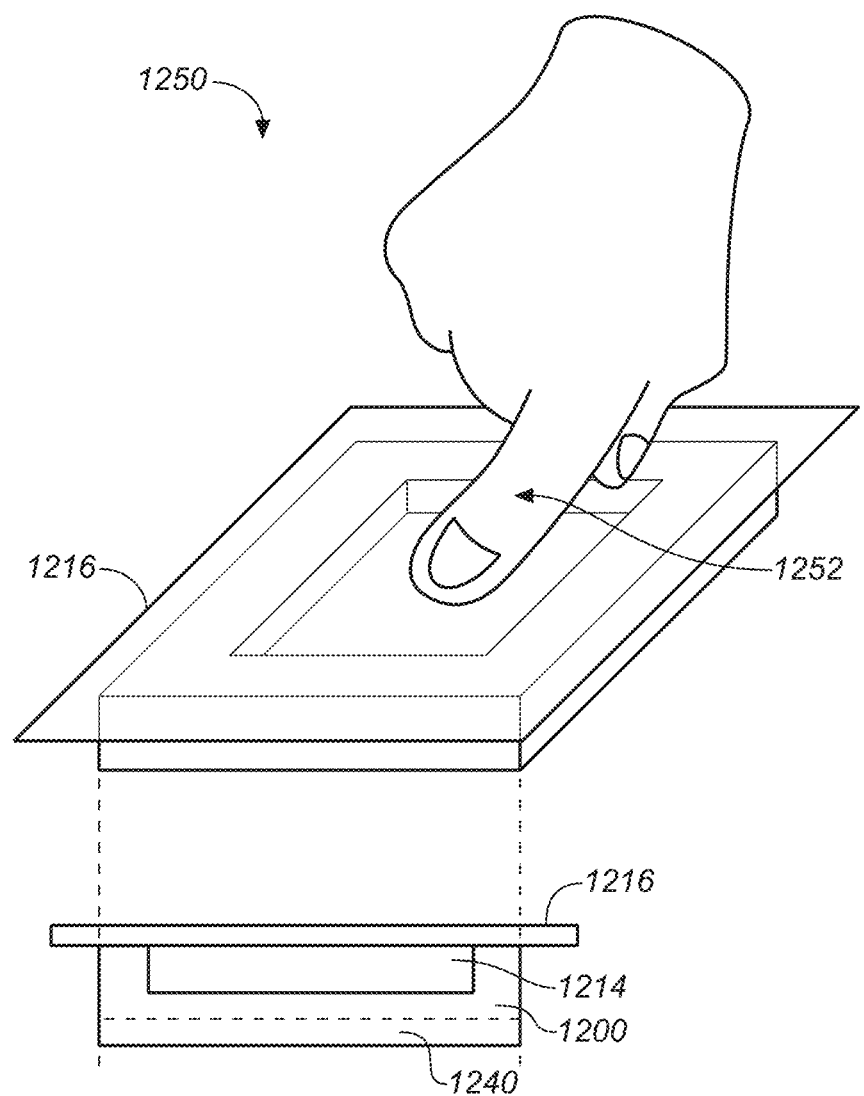
FIG. 12 illustrates a PMUT array used in an ultrasonic fingerprint sensing system, according to some embodiments.

FIG. 12 illustrates an embodiment of a PMUT array used in an ultrasonic fingerprint sensing system 1250. The fingerprint sensing system 1250 can include a platen 1216 onto which a human finger 1252 may make contact. Ultrasonic signals are generated and received by a PMUT device array 1200, and travel back and forth through acoustic coupling layer 1214 and platen 1216. Signal analysis is conducted using processing logic module 1240 (e.g., control logic) directly attached (via wafer bonding or other suitable techniques) to the PMUT device array 1200. It will be appreciated that the size of platen 1216 and the other elements illustrated in FIG. 12 may be much larger (e.g., the size of a handprint) or much smaller (e.g., just a fingertip) than as shown in the illustration, depending on the particular application.

In this example for fingerprinting applications, the human finger 1252 and the processing logic module 1240 can determine, based on a difference in interference of the acoustic signal with valleys and/or ridges of the skin on the finger, an image depicting epi-dermis and/or dermis layers of the finger. Further, the processing logic module 1240 can compare the image with a set of known fingerprint images to facilitate identification and/or authentication. Moreover, in one example, if a match (or substantial match) is found, the identity of user can be verified. In another example, if a match (or substantial match) is found, a command/operation can be performed based on an authorization rights assigned to the identified user. In yet another example, the identified user can be granted access to a physical location and/or network/computer resources (e.g., documents, files, applications, etc.)

In another example, for finger-based applications, the movement of the finger can be used for cursor tracking/ movement applications. In such embodiments, a pointer or cursor on a display screen can be moved in response to finger movement. It is noted that processing logic module 1240 can include or be connected to one or more processors configured to confer at least in part the functionality of system 1250. To that end, the one or more processors can execute code instructions stored in memory, for example, volatile memory and/or nonvolatile memory.

Figure 13:
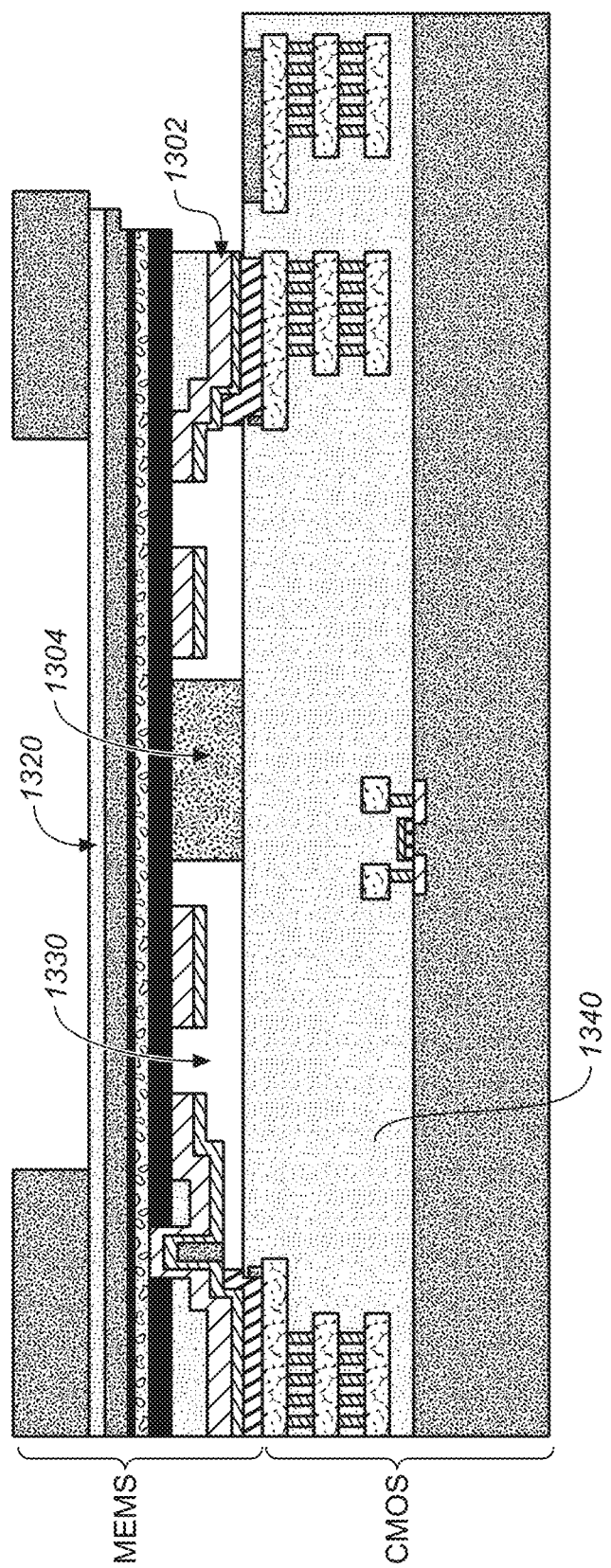
FIG. 13 illustrates an integrated fingerprint sensor formed by wafer bonding a CMOS logic wafer and a microelectromechanical (MEMS) wafer defining PMUT devices, according to some embodiments.

FIG. 13 illustrates an integrated fingerprint sensor 1300 formed by wafer bonding a CMOS logic wafer and a MEMS wafer defining PMUT devices, according to some embodiments. FIG. 13 illustrates in partial cross section one embodiment of an integrated fingerprint sensor formed by wafer bonding a substrate 1340 CMOS logic wafer and a MEMS wafer defining PMUT devices having a common edge support 1302 and separate interior support 1304. For example, the MEMS wafer may be bonded to the CMOS logic wafer using aluminum and germanium eutectic alloys, as described in U.S. Pat. No. 7,442,570. PMUT device 1300 has an interior pinned membrane 1320 formed over a cavity 1330. The membrane 1320 is attached both to a surrounding edge support 1302 and interior support 1304. The membrane 1320 is formed from multiple layers.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. A Piezoelectric Micromachined Ultrasonic Transducer (PMUT) device comprising:
   a substrate;
   an edge support structure connected to the substrate;
   a membrane connected to the edge support structure such that a cavity is defined between the membrane and the substrate, the membrane configured to allow movement at ultrasonic frequencies, the membrane comprising:
      a piezoelectric layer configured to generate an electric charge under stress such that the piezoelectric layer senses mechanical vibrations caused by an ultrasonic signal and produces the electric charge responsive to the stress of the piezoelectric layer; and
      first and second electrodes coupled to opposing sides of the piezoelectric layer and configured to collect the electric charge; and
   an interior support structure disposed within the cavity and connected to the substrate and the membrane, wherein the interior support structure contacts the edge support structure.

2. The PMUT device of claim 1, further comprising:
   a second interior support structure disposed within the cavity and connected to the substrate and the membrane.

3. The PMUT device of claim 1, wherein the interior support structure is non-centrally positioned within the cavity.

4. The PMUT device of claim 1, wherein the first electrode defines a continuous layer.

5. The PMUT device of claim 1, wherein the first electrode is a patterned layer.

6. The PMUT device of claim 1, the membrane further comprising:
   a mechanical support layer connected to the first electrode.

7. The PMUT device of claim 6, wherein the mechanical support layer defines a continuous layer.

8. The PMUT device of claim 6, wherein the mechanical support layer is a patterned layer.

9. The PMUT device of claim 1, wherein the piezoelectric layer defines a continuous layer.

10. The PMUT device of claim 1, wherein the piezoelectric layer is a patterned layer.

11. The PMUT device of claim 1, wherein the second electrode extends into the cavity and defines an area between the edge support structure and the interior support structure.

12. The PMUT device of claim 1, wherein the interior support structure is connected to the piezoelectric layer of the membrane.

13. The PMUT device of claim 1, wherein the PMUT device is substantially circular such that the edge support structure and the membrane are substantially circular.

14. The PMUT device of claim 1, wherein the PMUT device is substantially square-shaped such that the edge support structure and the membrane are substantially square-shaped.

15. The PMUT device of claim 1, wherein at least one of the first electrode and the second electrode is electrically coupled through the interior support structure.

16. The PMUT device of claim 1, the membrane further comprising:
   a third electrode coupled to the piezoelectric layer on an opposing side of the piezoelectric layer as the first electrode.

17. The PMUT device of claim 1, wherein the edge support structure is connected to an electric potential.

18. The PMUT device of claim 1, wherein the substrate comprises a CMOS logic wafer.

19. A Piezoelectric Micromachined Ultrasonic Transducer (PMUT) array comprising:
   a plurality of PMUT devices, wherein at least one PMUT device of the plurality of PMUT devices comprises:
      a substrate;
      an edge support structure connected to the substrate, wherein the edge support structure is connected to an electric potential;
      a membrane connected to the edge support structure such that a cavity is defined between the membrane and the substrate, the membrane configured to allow movement at ultrasonic frequencies, the membrane comprising:
         a piezoelectric layer configured to generate an ultrasonic wave responsive to receiving an electric charge by vibrating in an oscillatory fashion at a frequency related to the electric charge;
         first and second electrodes coupled to opposing sides of the piezoelectric layer and configured to apply the electric charge to the piezoelectric layer; and
         a mechanical support layer connected to the first electrode; and
      an interior support structure disposed within the cavity and connected to the substrate and the membrane, wherein the interior support structure contacts the edge support structure.

20. The PMUT array of claim 19, wherein the at least one PMUT device of the plurality of PMUT devices further comprises:
   a second interior support structure disposed within the cavity and connected to the substrate and the membrane.

21. The PMUT array of claim 19, wherein the interior support structure is non-centrally positioned within the cavity.

22. The PMUT array of claim 19, wherein the second electrode extends into the cavity and defines an area between the edge support structure and the interior support structure.

23. The PMUT array of claim 19, wherein the interior support structure is connected to the piezoelectric layer of the membrane.

24. The PMUT array of claim 19, wherein at least one of the first electrode and the second electrode is electrically coupled through the interior support structure.

25. The PMUT array of claim 19, wherein the substrate comprises a CMOS logic wafer.

26. The PMUT array of claim 19, wherein adjacent PMUT devices of the plurality of PMUT devices are electrically isolated.

27. The PMUT array of claim 19, wherein groups of adjacent PMUT devices of the plurality of PMUT devices are electrically connected, and wherein adjacent groups of adjacent PMUT devices are electrically isolated.

28. An image sensing system comprising:
a plurality of Piezoelectric Micromachined Ultrasonic Transducer (PMUT) devices, wherein at least one PMUT device of the plurality of PMUT devices comprises:
a substrate;
an edge support structure connected to the substrate;
a membrane connected to the edge support structure such that a cavity is defined between the membrane and the substrate, the membrane configured to allow movement at ultrasonic frequencies, the membrane comprising:
a piezoelectric layer configured to generate a first electric charge under stress such that the piezoelectric layer senses mechanical vibrations caused by an ultrasonic signal and produces the first electric charge responsive to the stress of the piezoelectric layer, and configured to generate an ultrasonic wave responsive to receiving a second electric charge by vibrating in an oscillatory fashion at a frequency related to the second electric charge;
first and second electrodes coupled to opposing sides of the piezoelectric layer, the first and second electrodes configured to collect the first electric charge from the piezoelectric layer and configured to apply the second electric charge to the piezoelectric layer; and
a mechanical support layer connected to the first electrode; and
an interior support structure disposed within the cavity and connected to the substrate and the membrane, wherein the interior support structure contacts the edge support structure; and
control logic electrically coupled to the plurality of PMUT devices, the control logic for sensing an image.

29. The image sensing system of claim 28, wherein the second electrode extends into the cavity and defines an area between the edge support structure and the interior support structure.

30. The image sensing system of claim 29, wherein at least one of the first electrode and the second electrode is electrically coupled through the interior support structure.

* * * * *